United States Patent
McKibben et al.

(10) Patent No.: US 6,316,017 B1
(45) Date of Patent: Nov. 13, 2001

(54) COMPOSITION AND APPARATUS USEFUL FOR ATTRACTING AND CONTROLLING INSECT PESTS

(75) Inventors: Gerald Hopkins McKibben; James Winfred Smith; William Lawrence McGovern, all of Starkville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 08/150,703

(22) Filed: Nov. 10, 1993

Related U.S. Application Data (63) Continuation-in-part of application No. 07/885,052, filed on May 11, 1992, now abandoned, application No. 07/885,052, which is a continuation of application No. 07/592,946, filed on Oct. 4, 1990, now abandoned, and a continuation-in-part of application No. 07/473,757, filed on Feb. 2, 1990, now Pat. No. 5,290,556.

(51) Int. Cl.[7] .................................................. A01N 25/10
(52) U.S. Cl. ........................ 424/410; 424/84; 424/405; 424/406; 424/407; 424/411; 424/419; 424/420; 424/421; 514/65; 514/531; 514/75
(58) Field of Search ............ 514/531, 65; 424/405–409, 424/84, 406, 410–413, 419–421; 524/77

(56) References Cited

U.S. PATENT DOCUMENTS

| | | | |
|---|---|---|---|
| 24,620 | * 7/1859 | Ellery et al. ............................ | 524/77 |
| 601,183 | * 3/1898 | Thum ..................................... | 424/411 |
| 1,545,005 | * 7/1925 | Meyer et al. ........................ | 424/419 |
| 2,311,911 | * 2/1943 | Swain et al. ............................ | 260/24 |
| 3,318,769 | 5/1967 | Folekemer et al. ................... | 514/144 |
| 3,350,329 | * 10/1967 | Scholl ..................................... | 260/8 |
| 3,655,129 | * 4/1972 | Seiner ................................... | 239/60 |
| 3,689,459 | * 12/1971 | Largman et al. ...................... | 424/410 |
| 3,803,303 | 4/1974 | McKibben et al. ..................... | 424/84 |
| 4,027,420 | 6/1977 | McKibben et al. ..................... | 424/84 |
| 4,237,113 | 12/1980 | Cardarelli ............................... | 424/78 |
| 4,369,176 | 1/1983 | Ott ......................................... | 424/84 |
| 4,808,615 | 2/1989 | Ott et al. ................................ | 514/89 |
| 4,818,525 | 4/1989 | Kamada et al. ..................... | 514/464 |
| 4,851,218 | 7/1989 | Hildebrandt et al. ................. | 424/84 |
| 4,889,710 | 12/1989 | Hagarty ................................. | 424/45 |
| 4,965,287 | 10/1990 | Stendel et al. ....................... | 514/531 |

OTHER PUBLICATIONS

Shearer et al. Citral in The Nassanoff Phermone of the Honey Bee. J. Insect. Physiol. vol. 12, 1513–1521, 1966.*
McKibben et al, "Identification of Feeding Stimulants for Boll Weevils from Cotton Buds and Anthers", J. Chem. Ecology 11 (9):1229–1238, 1985.
Warnaar, "Conjugated Fatty Acids from Latex of Euphorbia Lathyris", Phytochemistry 20:89–91. 1981.
Tumlinson et al, "Sex Pheromones Produced by Male Boll Weevil: Isolation, Identification, and Synthesis", Science 166:1010–1012. 1969.
Lloyd et al, "A Red Dye to Evaluate Bait Formulations and to Mass Mark Field Populations of Boll Weevils", J. Econ. Entomol. 61:1440–1444. 1968.
Daum et al, "Development of the Bait Principle for Boll Weevil Control: Cottonseed Oil, a Source of Attractants and Feeding Stimulants for the Boll Weevil", J. Econ. Entomol. 60:321–325. 1967.

(List continued on next page.)

Primary Examiner—Neil S. Levy
(74) Attorney, Agent, or Firm—M. Howard Silverstein; John D. Fado; Gail E. Poulos (57) ABSTRACT

The present invention describes a composition which includes a binder, a pigment, an insect toxicant, an insect feeding stimulant or a toxicant regeneration enhancer, and an ingredient which is both a filler and a thickener. The composition may be applied to a solid substrate to reproduce an article of manufacture which is both attractive and toxic to insect pests and therefore useful for insect control.

23 Claims, 4 Drawing Sheets

OTHER PUBLICATIONS

McLaughlin, "Development of the Bait Principle for Boll Weevil Control, II. Field–Cage Tests with a Feeding Stimulant and the Protozoan Mattesia grandis", J. Invert. Path 9:70–77. 1967.

Hunter et al, "The Mexican Cotton Boll Weevil", USDA Bur. Entomol. Bull. 51. 181 pp. 1905.

No. 2535 Merck Index 10th Edition.

No. 8315 Merck Index 10th Edition.

McKibben et al, "Air–Dropped Boll Weevil Bait Dispensers", MAFES Research Report 1(12).

Kydonieus et al, "Insect Suppression with Controlled Release Pheromone Systems", CRC Press 1:217–222. 1982.

* cited by examiner

COMPOSITION AND APPARATUS USEFUL FOR ATTRACTING AND CONTROLLING INSECT PESTS

This application is a continuation-in-part of application Ser. No. 07/885,052, filed May 11, 1992 now abandoned, which is herein incorporated by reference. Application Ser. No. 07/885,052 is a File Wrapper Continuation of application Ser. No. 07/592,946 filed Oct. 4, 1990 which is now abandoned. This application is also a continuation-in-part application of application Ser. No. 07/473,757, filed Feb. 2, 1990, now U.S. Pat. No. 5,290,556, issued Mar. 1, 1994, which is herein incorporated by reference.

BACKGROUND OF THE INVENTION

Boll Weevils, *Anthonomus grandis* Boheman (Coleoptera: Curculinidae), are insect pests that feed on cotton plants causing serious damage to the plants and reducing harvest yield. Since shortly after the entry of the cotton boll weevil, *Anthonomus grandis* (Boheman), into the southwestern United States in the early part of this century, baits have been investigated as a control measure for this destructive pest. Previous attempts have been made to trap, kill, or destroy the boll weevil.

Hunter et al (USDA Bur. Entomol. Bull., v. 51, 181 pp., 1905) tested a mixture containing molasses as a feeding stimulant with calcium arsenate. More recently, after the discovery that crude cottonseed contained feeding stimulants and attractants for this species (Daum et al, J. Econ. Entomol., v. 60, 321–325, 1967), cottonseed oil—water emulsion bait formulations were used to infect the insects with a protozoan disease (McLaughlin, J. Invert. Path., v. 9, 70–77, 1967) and to mass-mark field populations (Lloyd et al, J. Econ. Entomol., v. 61, 1440–1444, 1968).

Since the discovery and synthesis of the male boll weevil aggregating pheromone (Tumlinson et al, Science, v. 166, 1010–1012, 1969), the use of baits for controlling the boll weevil has been investigated from time to time, primarily at the Boll Weevil Research Unit at Mississippi State. Most of the baits investigated previously were designed to be applied to the cotton foliage when cotton buds, the natural food for the weevils, were readily available. Competition from the buds as well as application problems and susceptibility to rain wash-off, prevented the baits from being effective enough to be considered a viable control method.

U.S. Pat. No. 3,803,303 describes polymeric compositions for attracting boll weevils using the male sex pheromone, Grandlure, in combination with polyethylene glycol and a toxicant such as p-dichlorobenzene. Additionally, the plant attractants caryophylline oxide and beta-bisabalol were used. The attractant was applied to cotton dental rolls.

U.S. Pat. No. 4,027,420 discloses a bait formulation containing Grandlure absorbed into cigarette filters or cotton dental rolls and containing DDVP (o,o-Dimethyl, 2, 2-dichlorovinyl phosphate). The filters were attached to an airdropped device that was designed to lodge in the foliage cotton plants.

Like all baits for the boll weevil, the approach disclosed in the two patents mentioned above was difficult to evaluate effectively, but did not compare favorably with pheromone baited traps.

The prior art uses of toxic baits have also been in various water-based forms. These bait formulations have been subject to dissolution, dilution, or wash-off by rain. With Grandlure, the application of liquid baits around cotton fields early and late in the season was attempted, likewise with limited success due to the lack of a proper formulation and dispensing system for Grandlure (unpublished).

There is a need for a means to kill chewing insects pests that does not suffer the disadvantages of the prior art insecticide traps or baits described above and that is species specific and thus protecting the insect species that are beneficial to crop plants.

SUMMARY OF THE INVENTION

Objects of the present invention include providing insect control which is highly effective, and yet: inexpensive, easy to use, maintenance free, environmentally safe, provides an unlimited killing capacity, species specific, permits the use of less insecticide per unit area than conventional methods, eliminates the need for frequent pesticide reapplication, environmentally stable (e.g. durable and free from rain wash-off), ingestible by insects and yet safe to humans, animals and non-targeted insects.

One aspect of the present invention relates to compositions, apparatus, and methods for attracting and killing or destroying chewing pests such as armyworm, boll weevil, boll worm, loopers, cutworms, and the larvae and adults of many other leptodopterdus and coleopterous pests.

A composition of the present invention comprises:
a binder,
a pigment,
an insect toxicant,
an insect feeding stimulant, and
an ingredient which is both a filler and thickener
(e.g. as an essentially homogeneous mixture).

Still another composition of the present invention comprises:
a binder,
a pigment,
an insect toxicant,
a toxicant regeneration enhancer, and
an ingredient that is both a filler and thickener
(e.g. as an essentially homogeneous mixture).

These compositions can be incorporated in an article of manufacture comprising a substrate having thereon a coating of the aforementioned composition.

Another aspect of the present invention is a process comprising applying the aforementioned compositions to a substrate and permitting an insect to come in contact with and/or feed upon said composition. Insects coming into contact with the aforementioned insect attracticide composition, for even a short period of time (e.g. a few seconds), absorb a lethal dose of the toxiant or become stuck to the surface and die. Insects (e.g. boll weevils) that feed on said composition with the toxicant die in a short time (e.g. a few minutes). Insects that absorb a lethal dose (e.g. through tarsal contact) die in a relatively longer time (e.g. 30 minutes to 1 hour).

The present invention is effective against a wide variety of insect, such as for example: armyworm, boll weevil, boll worm, loopers, cutworms, larvae of many other lepodopterous and coleopterous pests, etc.

DESCRIPTION OF THE PREFERRED EMBODIMENTS

The compositions of the present invention include a binder, such as various synthetic and natural resins typically used in paints and coatings, though modified to cause the coated surface to be friable enough to allow insects to bit off and ingest the material, while still maintaining the structural integrity of the coating. This is achieved in the present invention by including an ingredient which is both a filler and thickener, e.g. an inert mineral clay, such as attapulgite. Examples of binders useable in the present invention include one or more of shellac, acrylics, epoxies, alkyds, polyurethanes, linseed oil, and tung oil.

The compositions of the instant invention also include a pigment. The color of the pigment is selected according to which color(s) will attract the targeted insect(s). For example, where a green color is desired, it is preferred to use "Lime green pigment 25717" from Carolina Color Corporation, Salisbury, N.C. Other pigments which may be used in the present invention are described in the *Modem Plastics Encyclopedia* published by McGraw Hill, New York, N.Y.

Also included in the compositions of the present invention is at least one insect toxicant. The insect toxicant(s) is/are selected based upon the type of insect(s) to be controlled or eradicated. Insect toxicants useable in the present invention include one or more of pyrethoroid or organophosphorus insecticides, for example. Some examples of insect toxicants useable in the present invention are cyfluthrin, permethrin, cypermethrin, bifinthrin, fenvalerate, flucythrinate, azinphosmethyl, methyl parathion, malathion, etc.

One composition of the instant invention also includes at least one insect feeding stimulant such as at least one feeding stimulant selected from the group consisting of one or more of crude cottonseed oil, fatty acid esters of phytol or fatty acid esters of geranyl geraniol or fatty acid esters of other plant alcohols, and cotton plant extracts which stimulate insect feeding.

Furthermore, one composition of the instant invention includes at least one ingredient which enhances regeneration of toxicant on the surface of the dried coating. The toxicant regeneration enhancer useable in the present invention includes one or more of fatty acids and any vegetable oil such as for example olive oil, soybean oil, corn oil, safflower oil, canola oil, etc.

Also included in compositions of the present invention is an ingredient which is both a filler and thickener, such as one or more of mineral clays (e.g. attapulgite) and organic thickeners. More specifically, such organic thickeners may be selected from the group consisting of one or more of methyl cellulose and ethyl cellulose.

Optionally, the compositions of the present invention may include a solvent(s) when it is desired that said compositions be in the form of a liquid, where the use is to employ said compositions in a manner similar to a paint, e.g. by brushing, dipping, rolling, spraying, or otherwise applying the compositions of the present invention to substrates on which the user wishes to provide an insecticidal coating and subsequently permitting an insect to feed upon said composition. The solvent(s) to be used in the instant invention is/are selected so as to solubilize, or substantially solubilize, the other ingredients of the composition. Solvents which may be used include one or more of: ethyl alcohol, methyl alcohol, chlorinated hydrocarbons, petroleum solvents, turpentine, and xylene.

The compositions of the present invention may also include an insect attractant. Examples of such attractants include one or more of insect pheromones (e.g. Grandlure), cotton plant extracts (e.g. Beta-caryophyllene and Beta-bisabalol), volatile plant compositions and synthetic insect attractants. Advantageously, those compositions of the present invention which include a pheromone, provide a controlled release of the pheromone while providing a surface which insects can cling to and feed upon. The controlled release may be augmented by incorporation of certain high-molecular weight polymers which regulate the rate of evaporation of the pheromone. Alternatively to incorporating the insect attractant in the composition, the attractant may be omitted from the composition and instead deployed in a separate dispenser positioned adjacent to the composition of the present invention (e.g. in a separate dispenser affixed to a stake coated with the composition of the present invention). For example, when Grandlure is utilized it may constitute from about 0.02 to about 1 weight percent of the composition, preferably from about 0.5 to about 0.4 weight percent, and most preferably from about 0.1 to about 0.3 percent. When Beta-caryophllene and/or Beta-bisabalol are utilized, it/they may constitute from about 0.2 to about 10 weight percent of the composition, preferably from about 0.5 to about 4 weight percent and most preferably from about 1.0 to about 3 weight percent.

The following Table 1 illustrates exemplary proportions of ingredients for a liquid (i.e. containing a substantial portion of solvent) composition of the present invention:

TABLE 1

| Ingredient | Exemplary range of proportions of ingredients (in % by weight), about: | Preferred proportions (in weight %), about: | Most preferred proportions (in weight %), about: |
|---|---|---|---|
| Shellac | 17 to 35 | 23 to 34 | 24 to 31 |
| Ethyl alcohol | 23 to 64 | 45 to 57 | 48 to 57 |
| Lime Green Pigment 25717, from Carolina Color Corp Salisbury, NC | 1 to 12 | 4 to 7 | 6 to 7 |
| Cyfluthrin | 0.1 to 4.6 | 0.1 to 1.7 | .14 to 1.7 |
| Crude Cottonseed Oil | 1 to 23 | 1 to 3 | 2.4 to 3 |
| Clay filler | 1 to 17 | 5 to 17 | 9.5 to 14.3 |

The compositions of Table 1 may be employed analogously to a paint, i.e. said compositions, in the form of an essentially homogeneous mixture, may be applied to a surface or substrate on which an insecticidal coating is desired and the solvent (i.e. ethyl alcohol) will evaporate, leaving an essentially solid (and essentially homogeneous) coating.

Table 2 illustrates exemplary proportions of ingredients for another set of liquid (i.e. containing a substantial portion of solvent) composition of the present invention:

TABLE 2

| Ingredient | Exemplary range of proportions of ingredients (in % by weight), about: | Preferred proportions (in weight %), about: | Most preferred proportions (in weight %), about: |
| --- | --- | --- | --- |
| Shellac | 10 to 35 | 15 to 34 | 15 to 31 |
| Ethyl alcohol | 23 to 64 | 45 to 57 | 48 to 57 |
| Lime Green Pigment 25717, from Carolina Color Corp. Salisbury, NC | 1 to 12 | 4 to 7 | 6 to 7 |
| Toxicant | 0.1 to 4.6 | 0.1 to 1.7 | .14 to 1.7 |
| Fatty Acid or Vegetable Oil | 1 to 23 | 1 to 23 | 10 to 20 |
| Clay filler | 1 to 20 | 5 to 18 | 9.5 to 18 |

Again, the compositions of Table 2 may be employed analogously to a paint, i.e. said compositions, in the form of an essentially homogeneous mixture, may be applied to a surface or substrate on which an insecticidal coating is desired and the solvent (i.e. ethyl alcohol) will evaporate, leaving an essentially solid (and essentially homogeneous) coating.

Table 3 illustrates exemplary proportions of ingredients for one type of essentially solid coating compositions of the present invention:

TABLE 3

| Ingredient | Exemplary range of proportions of ingredients (in % by weight), about: | Preferred proportions (in weight %), about: | Most preferred proportions (in weight %), about: |
| --- | --- | --- | --- |
| Shellac | 25 to 60 | 25 to 50 | 44.6 |
| Lime Green Pigment 25717, from Carolina Color Corp Salisbury, NC | 5 to 30 | 5 to 25 | 23.9 |
| Cyfluthrin | 1 to 5 | 1 to 4 | 3.7 |
| Crude Cottonseed Oil | 5 to 15 | 5 to 15 | 9.4 |
| Clay filler | 10 to 40 | 10 to 30 | 18.4 |

Another type of essentially solid coating compositions of the present invention is illustrated in Table 4:

TABLE 4

| Ingredient | Exemplary range of proportions of ingredients (in % by weight), about: | Preferred proportions (in weight %), about: | Most preferred proportions (in weight %), about: |
| --- | --- | --- | --- |
| Shellac | 25 to 60 | 25 to 50 | 44.6 |
| Lime Green Pigment 25717, from Carolina Color Corp Salisbury, NC | 5 to 30 | 5 to 25 | 23.9 |
| Toxicant | 1 to 5 | 1 to 4 | 3.7 |
| Fatty Acid or Vegetable Oil | 1 to 23 | 1 to 23 | 10 to 20 |
| Clay filler | 10 to 40 | 10 to 30 | 18.4 |

Another aspect of the instant invention relates to an article of manufacture comprising a substrate having thereon a composition as described herein above. The present invention encompasses any of a wide variety of substrates. Choice of a substrate will depend on factors such as ease of use, cost, and ease of deployment. Preferably, said substrate may take the form of a cylinder made from, for example, plastic, bamboo, or paper, having an outer diameter of from about ⅓ inch to about 1½ inches, and from about 2 feet to about 4 feet in length. Native female boll weevils have shown a preference for dowels of about 9 millimeters (mm) (0.35 inches [in]) diameter in terms of contact time, but not in terms of the percent of the total number responding. The mean contact time for the 9 mm of 3.59 minutes was significantly higher than the time for all other sizes. This preference is perhaps related to their ovipositional preference for cotton buds of approximately 8 mm diameter. Native male boll weevils have not shown significantly different mean contact time or mean percent of total response, for any of various dowel diameters tested, although they did display some preference for a 9 mm dowel (which may be related to their feeding preference). Laboratory males and females showed a less pronounced preference for any size dowel in terms of contact time and percent of total number responding, except that the laboratory females showed a preference, in terms of percent of total number responding, to the 9 mm dowel, but the mean was not significantly different from the other means. In greenhouse tests, mixed sex weevils preferred vertically oriented dowels to dowels in other orientations. No statistical analysis was done on these data.

In laboratory assays, there were apparent trends toward a preference for the 60° and 90° angles in terms of both contact time and percent of total number responding for males and females alike, but differences in the means were not significant. Regression analysis of both contact time and percent of total number responding vs angle for both males and females likewise did not yield any significant difference.

Figure 2:
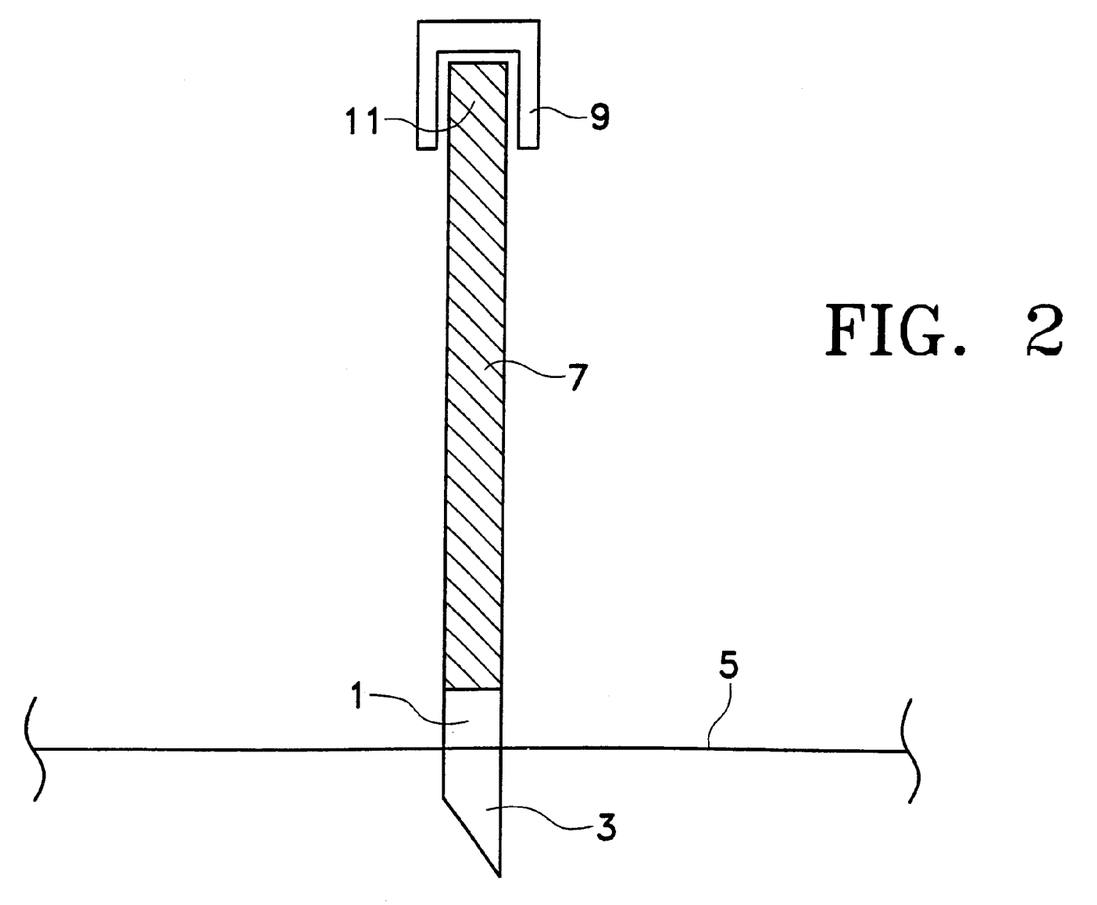
FIG. 2 depicts a manufacture of the present invention including a cylindrical substrate (stake) having a coating and cap thereon.

FIG. 2 illustrates an article of manufacture of the present invention, which includes a substrate 1. While substrate 1 is shown in a cylindrical shape, it may be any variety of configurations and sizes. A first end 3 of substrate 1 may be pointed (FIG. 2) to facilitate inserting the substrate into ground 5. The substrate has thereon coating 7, a composition of the present invention. Coating 7 may be formed by holding first end 3 of substrate 1 and dipping the reminder of the substrate in a liquid composition of the present invention. Optionally, the article of manufacture of the present invention may include cap 9, e.g. a polyvinyl chloride (PVC) cap (shown cut-away) on second end 11 of substrate 1. Said cap may be produced in accordance with the aforementioned co-pending application Ser. No. 07/473, 757 filed Feb. 2, 1990, now U.S. Pat. No. 5,290,556, issued Mar. 1, 1994, by Gerald McKibben et al. More specifically, said cap is a bait-insecticide composition comprising: a polymer, at least one insect pheromone, at least one insect pheromone, at least one insect feeding stimulant, and an insect toxicant.

The process of the present invention comprises applying a composition as described herein above to a substrate, and permitting an insect to come in contact with and/or feed upon said composition. In a preferred embodiment, the compositions of the present invention are applied to a stake which is driven into the ground in an essentially vertical position, in a location where it is desired to control or eradicate insects.

The following examples are given to further illustrate the invention and are not intended to limit the scope of the invention as defined by the claims.

EXAMPLE 1

The following components were combined to form a thickened mixture:

|  | Percent by Weight |
|---|---|
| Natural Shellac | 25.8 |
| Denatured Ethanol | 38.9 |
| Pigment (Lime green pigment 25717 from the Carolina Color Corp., Salisbury, North Carolina) | 4.5 |
| Cyfluthrin Wettable Powder, 20% a.i. (toxicant) | 8.9 |
| Crude Cottonseed Oil (feeding stimulent) | 11.5 |
| Grandlure (synthetic pheromone) | 0.30 |
| Polyethylene glycol 6000 | 1.2 |
| Silica (thickener) | 8.9 |

The mixture was applied to wooden stakes by dipping. Approximately 50 grams was applied to each of three ⅞ inch diameter wooden stakes. After drying, the stakes were driven into the ground near a cotton field. Aluminum pans were placed underneath to facilitate counting of dead boll weevils. In three days, the three stakes killed 367, 236, and 161 boll weevils, or a total of 764. Three similarly prepared stakes were placed in another location. Thirteen days later, a total of 375 dead boll weevils were counted in the three kill pans. These results show that stakes treated in this manner effectively attract and kill boll weevils. While not wishing to be bound by any theory, it is believed that: the weevils are attracted to the treated stakes by both the pheromone and by the green color, and that the feeding stimulant induced them to feed. It is also believed that the round shape and diameter of the stake are factors in inducing the weevils to remain in contact with the surface long enough to absorb a fatal dose of insecticide. These stakes compare favorably with pheromone baited traps, while being less expensive and requiring no service once deployed.

EXAMPLE 2

The following components were combined to form a thickened mixture:

|  | Percent by Weight |
|---|---|
| Shellac | 15.7 |
| Ethyl Alcohol | 43.3 |
| Pigment (Lime green pigment 25717 from the Carolina Color Corp, Salisbury, NC) | 2.6 |
| Cyfluthrin | 2.8 |
| Fatty Acid or Vegetable Oil | 18.0 |
| Siliceous Clay | 2.8 |

Figure 4:
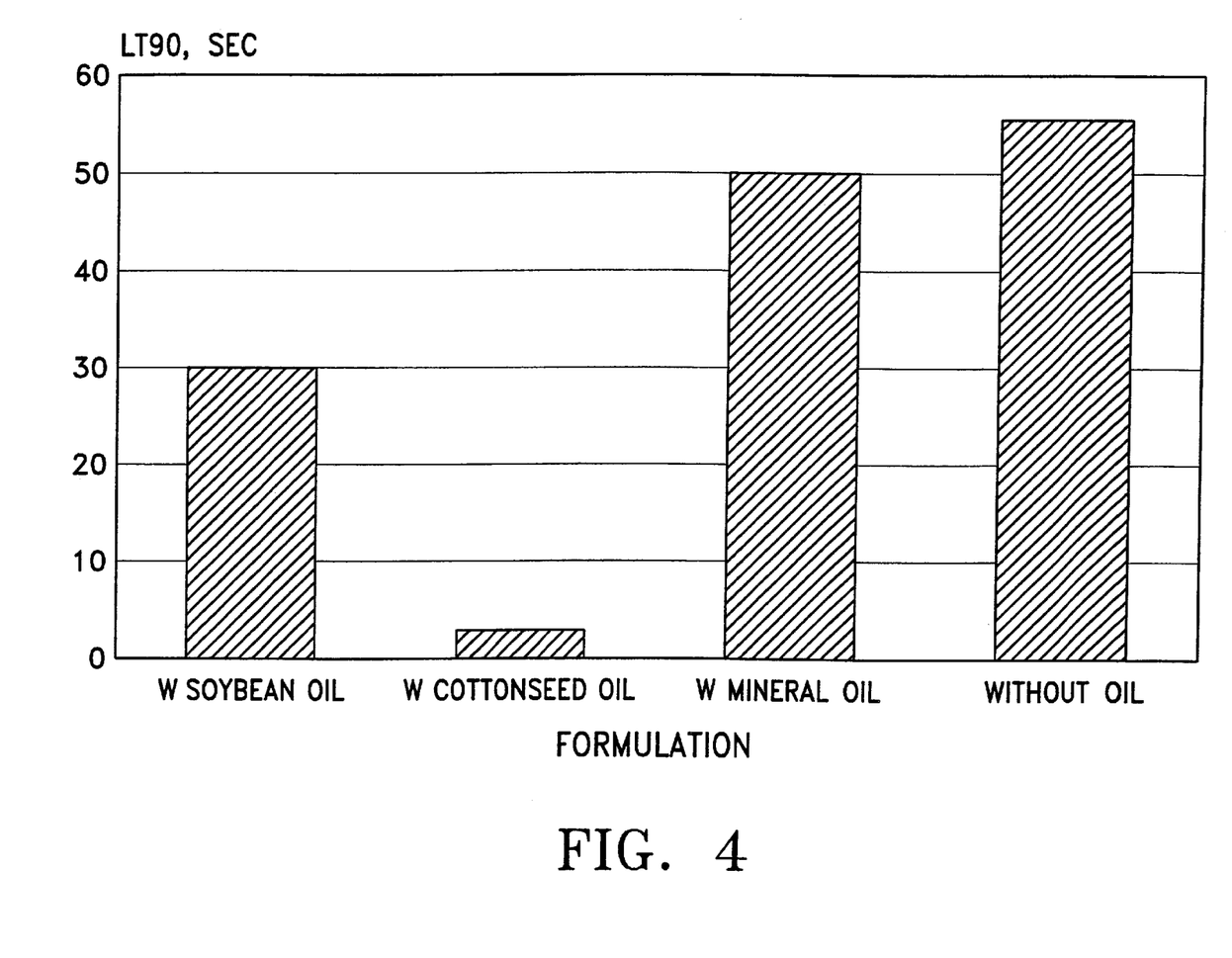
FIG. 4 is a graph of the toxicity of different coatings with various oils.

The coating was prepared by first dissolving dry shellac in ethyl alcohol. When completely dissolved, the other ingredients were blended in no particular order. Four (4) different coatings were prepared which included different fatty acids (listed in Table 5) and vegetable oils (see FIG. 4).

8 grams of each coating were applied to each of 5 inch×5 inch glass slides. Each coating was allowed to spread out to cover a circle 9 cm in diameter previously marked on the slides. The slides were then allowed to dry.

For bioassays, one boll weevil was confined at a time to the dry coating for 2, 4, 8, 16, or 32 seconds. The weevils were held in clean paper cartons at room temperature for 24 hour mortality counts. There were 10 insects per replicate, with 3 to 6 replicates. LT (lethal time) values were calculated using the SAS PROBIT procedure (SAS Institute, Cary, North Carolina). An LT90 value of 5 seconds, for example, means that 5 seconds exposure to the coating was sufficient to kill 90% of the treated insects. The mortality was measured after 24 hours, but the LT values are the exposure times.

The results show that the addition of a fatty acid to the composition dramatically decreases the LT90 (See Table 5) when compared to the formulation without fatty acid and oil. Furthermore, the $LT_{90}$s of the various fatty acid formulations were substantially less when compared to the formulation containing the feeding stimulant cottonseed oil. The vegetable oil, soybean oil, also decreased the $LT_{90}$ of the composition when compared to compositions with no oil or mineral oil.

TABLE 5

TOXICITY TO BOLL WEEVILS
COATINGS WITH VARIOUS FATTY ACIDS

| ACID | $LT_{90}$, SEC |
|---|---|
| Myristic | 0.5 |
| Lineoleic | 0.5 |
| Lauric | 0.5 |
| Lineolenic | 0.9 |
| Stearic | 1.0 |
| Palmitic | 2.3 |
| Oleic | 2.5 |

While not wishing to be bound by any theory it is believed that: the mixture of fatty acids or vegetable oils with an alcoholic shellac solution and a siliceous clay produces a mixture which is both a suspension and an emulsion. The fatty acids in the mixture form interconnected passages when the film is dried if a siliceous clay is added before drying. The degree of interconnection can be controlled by varying the concentrations of fatty acids and clay. It is the interconnecting canals or passages that are responsible for the transport of the oil-soluble active ingredient to the surface of the dried film. As the toxicant is lost on the surface due to mechanical removal or chemical degradation, more toxicant is transported to the surface via these interconnected passage ways. Therefore the addition of fatty acids to the mixture enhances regeneration of toxicant on the surface of the coated substrate.

EXAMPLE 3

The purpose of this example is to show: (1) the effectiveness of the coatings of the present invention; and, (2) the utilization of coatings of the present invention with PVC plastisol containing formulations.

Formulations of PVC Plastisol Containing Composition

A basic PVC plastisol was prepared by blending a mixture of Geon 100–130 (B.F. Goodrich) with dioctyl phthalate (DOP) in a weight ratio of 6:4. To this mixture were blended in a pigment (5% w/w), Grandlure (0.428% w/w), toxicant (Cyfluthrin: Cyan (4-fluoro-3-phenoxyphenyl) methyl 3-(2, 2-dichloroethenyl)-2-dimethyl-cyclopropanecarboxylate—20% wettable powder) at 2% active ingredient (a.i), and a feeding stimulant at 5% by weight. The feeding stimulant used was either phytol dodecanoate (McKibben et al., 1985, J. Chem. Ecol. 11: 1229–1238) or crude solvent extracted cottonseed oil. The pigment was either titanium dioxide or a lime green PVC pigment. PVC baits were prepared by dipping heated (180°) metal molds into the plastisol for from 15 to 30 seconds. The molds were withdrawn, held for 30 seconds to 1 minute to permit the PVC to heat and cure on the surface, and then plunged into cold water. After cooling, the PVC bait was removed from the molds, which were previously sprayed with a silicone product to aid removal. Molds used were wither 6 mm diameter stainless steel rods (test 1) or cone-shaped brass measuring 7 cm×2.5 cm diameter (all other tests).

Stake Coating (A Composition of the Present Invention)

The stake coating consists of Temp (20 weight % cyfluthrin) wettable powder at 2 weight % a.i., lime green pigment (5 weight %), and crude cottonseed oil (12 weight %) in a shellac base. The shellac was prepared by dissolving dry shellac in denatured alcohol at a concentration of 360 grams/liter. Application to the stakes was by dipping or brushing.

Laboratory Assays

Preliminary laboratory feeding assays were done by confirming 10 mixed sex, laboratory reared weevils in a petri dish containing 2 of the PVC 6 mm PVC bait pellets without a toxicant. Observations were made to determine the tendency of the boll weevils to orient to the pellets and to mount and feed on them.

Field Tests

A preliminary field test was done in Monroe Country, Miss. with the 6 mm PVC pellets. Twenty pellets were placed along a creek bank in a good boll weevil hibernation site bordering a cotton field. Placement of the pellets alternated between ground placement and ⅓ meter high on wire surveyor's stakes. At the end of this test the pellets were brought into the laboratory for examination for feeding damage. Feeding response was assessed by examining for feeding damage.

Field tests using the 7 cm×2.5 cm cones were done in Oktibbeha, Webster, Clay and Monroe counties, Miss. and near Vero Beach, Fla. The cones were placed on either bamboo (ca. 6 mm diameter) or wooden stakes (6 mm–24 mm diameter) driven vertically into the ground. In the Vero Beach test, a single row of 44 bait devices was deployed in a straight line, 15 meters (m) apart between 2 cotton fields that had been disked under approximately 2 weeks prior to the test. Twenty-four of the bait stations had kill pans underneath, the other 20 did not. There were 10 survey traps in the area, 3 of which were within 30 m of the bait stations, the others from 50 to 300 m. For the stake size test, hardwood dowels 1 m long were used. Three replicates of 10 diameters were arranged 6 m apart in a circle in a randomized block design. The diameters used were 3, 5, 6, 8, 9 11, 12, 15, 18 and 21 mm.

Pans of aluminum or steel were placed underneath the bait devices to facilitate counting of the dead boll weevils. Plain water or water with a wetting agent was used in the pans to prevent ants from removing dead weevils. Heights of the stakes was ca. ⅔ to 1 m.

In the laboratory, boll weevils readily oriented to and fed on the PVC bait pellets. In the preliminary field tests all but one of the pellets. In the preliminary field tests all but one of the pellets placed on wire stakes showed feeding damage at the end of test period. Several boll weevils were observed feeding on the pellets during this time period. None of the pellets placed on the ground had feeding damage.

Large numbers of overwintering boll weevils were observed flying to and alighting on the bait devices. During the peak emergence period the counts of dead boll weevils in the kill pans reached 100 to 150. Observations of the PVC cones placed on uncoated stakes revealed that many of the boll weevils responding remained on the stake without moving upward to the bait cone and were thus unaffected by the insecticide. Once the stakes were coated with the aforementioned composition of the present invention, the effectiveness of the devices increased dramatically. The mean time boll weevils remained in contact with the stake or PVC cone was 4.90 minutes +/−1.6. In the laboratory, less than 1 minute contact was sufficient to kill 100%. On calm days (wind gust less than 2 knots), 61% of the boll weevils alighting on the devices fell into the kill pans. On days with light to moderate winds (5–6 knots), only 38% of the weevils alighting on the devices fell into the pans. During the peak dispersal periods, when cotton fields were defoliated or on warm days after the killing frost, the kill pans often has 200–300 dead weevils/day.

Figure 1:
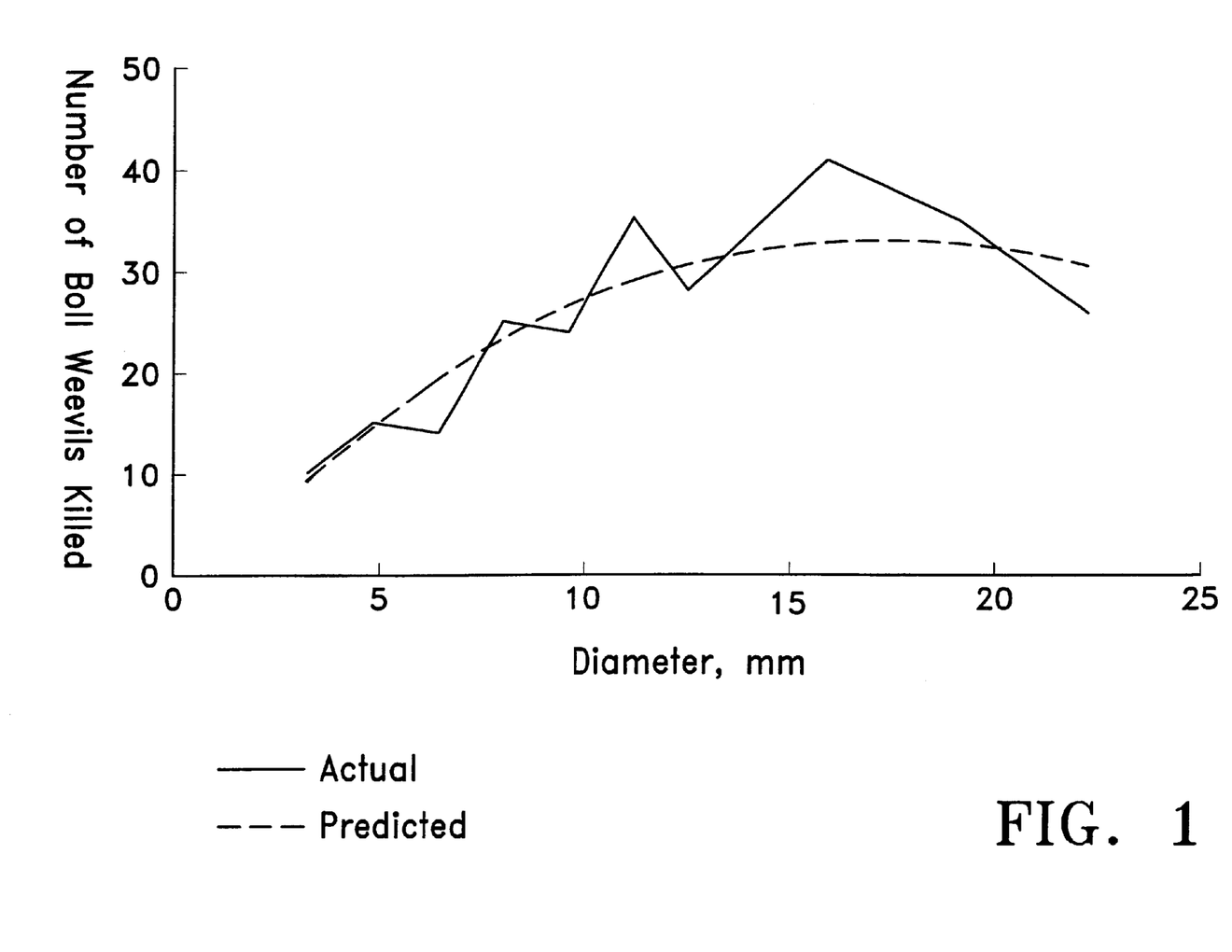
FIG. 1 is a graph of both actual and predicted number of boll weevils killed versus stake diameter (in millimeters), illustrating the effect of various stake diameters on the number of boll weevils killed.

Results of the stake size test are shown in FIG. 1. There was an increase in response, as measured by kill pan counts, with increasing stake diameter until the diameter reached about 15 mm, after which the response decreased. The regression equation for number killed ($P \leq 0.001$, $R^2 = 0.86$; 2/7 df) was:

$$Y = 261.60 e^{-2.213(x)} X^{1.484} \quad \text{[Eqn. 1]}$$

where:

Y=number killed, and;

X=stake diameter in millimeters.

This equation is graphed as a dashed line in FIG. 1 (i.e. referred to as "predicted").

Average weevil kill with attract-and-kill devices and capture in traps, for tests conducted in Vero Beach, Fla., are listed in Table 6:

TABLE 6

| | AVERAGES | |
|---|---|---|
| DAY | WEEVILS/KILL PAN (Present Invention) | WEEVILS/SURVEY TRAP |
| 1 | 16.2 | 3.0 |
| 2–6 | 70.0 | 13.90 |
| 7–13 | 5.4 | 1.25 |
| 14–21 | 0.42 | 0.12 |

These averages clearly indicate that the composition of the present invention is superior to the survey traps. The total kill after 21 days in the Vero Beach test for the 24 bait devices with kill pans was 1,809. Estimating the kills for the 20 devices without kill pans as equal to those with pans, the total for the 21 day period was 3,316. Correcting for the previously mentioned bias in kill pan counts vs. actual number killed and using the more conservative of 61% (actual number=pan count/1.61), gives a total estimate of 5,436 weevils killed.

Since toxicity of the cyfluthrin coating to the boll weevil was so great, only a short exposure was necessary to kill the insect. Thus feeding was secondary in importance to contact time. Though our observations showed that those insects that fed died much sooner than those that did not, exposure times in the laboratory of only a few seconds to freshly coated stakes was sufficient to kill 100% of affected insects whether they fed or not. Thus the device does not depend on feeding to be effective.

We believe that the new bait devices are a promising control method for the boll weevil, particularly during the early and late seasons. It is well known by those working with Grandlure baited traps that boll weevils appear to be especially responsive to the pheromone during these time periods. The response to the pheromone during the mid-season, reproductive period is somewhat lessened because of the competition from ale boll weevils. The use of a bait during this period has never showed much promise because of this factor and because of the ready availability of the insect's natural food, squares and small bolls of the cotton plant. In fact, response to the early baits increased with the decrease in the available food supply (McLaughlin, 1967, supra). Since the device we are working with does not depend on feeding, it may also be effective during the reproductive period. Another drawback with the early baits used was the time when they were effective in the field due to drying and to wash-off by rain (Daum et al, 1967, supra). The present system is apparently not affected by rainfall. Ease of application is another advantage over previous baits. Cost of the devices will be less than the cost of a trap.

EXAMPLE 4

This new bait stick is a viable alternative to the more than 300 million dollar annual losses to the cotton industry and cost to control the boll weevil.

The bait stick is made up of two parts: a cap and a wooden stake. The cap contains Grandlure, the pheromone which attracts boll weevils. The cap is formed from a mixture of plastic, green pigment (already proven to attract weevils), a sex pheromone called Grandlure (another attractant), a feeding stimulant (to entice them to eat the bait), and an insecticide: cyfluthrin.

The wooden sticks were coated with the composition described in Example 1 hereinabove. A PVC cap, as described in Example 3, was placed on top of each wooden stick.

A large field test is being conducted in Mississippi to evaluate the boll weevil bait stick as a suppression tool for use in boll weevil management/eradication programs. The test is replicated in three locations representing three cotton production areas os the state. These areas are the south Delta, central Delta, and hill region. Within each location three treatments will be randomly assigned to contiguous 250 acre blocks of cotton.

Analysis of differences are based on pheromone trap catches and square (flower bud) examinations.

Table 7 compares the treated and untreated areas and shows percent reduction in trap catch.

TABLE 7

BOLL WEEVIL BAIT STICK TEST
Three Locations

| LOCATION | BBS @ 1/ACRE | NUMBER BBS |
|---|---|---|
| Monroe County, MS | 6.80 | 21.75 |
| Sharkey County, MS | 8.70 | 18.38 |
| Carrol County, MD | 6.70 | 7.70 |

Number = Accumulation per trap since BBS deployed
BBS = Boll Weevil Bait Stick
Percent reduction of treated vs. untreated through August 15
Monroe County 69%
Sharkey County 53%
Carrol County 13%

Figure 3:
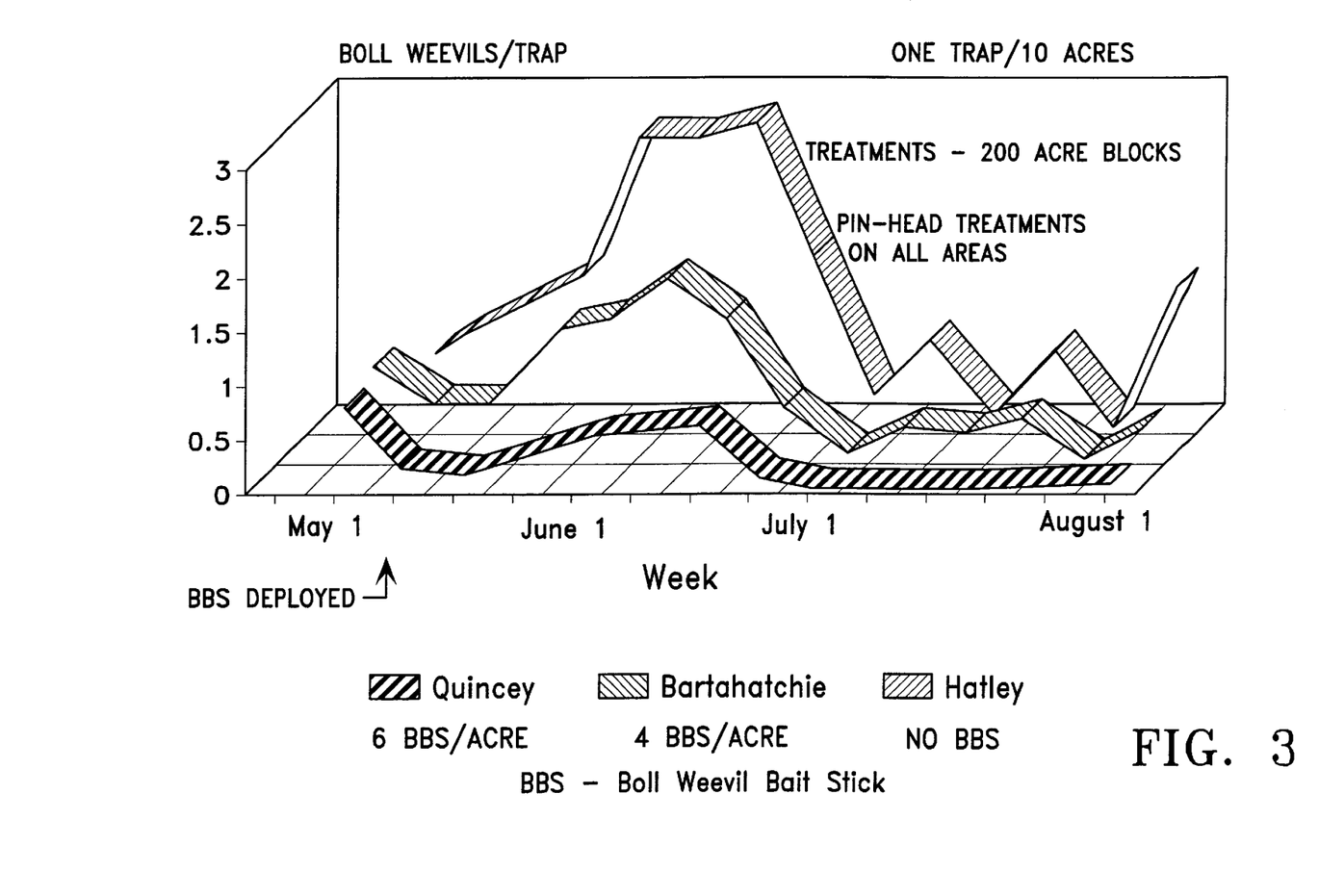
FIG. 3 is a graph of boll weevils per trap versus time (in weeks), for data obtained in instant example 4.

FIG. 3 shows weekly trap catches at three locations in Monroe County. Hatley was the check area and had no bait sticks. The Quincey area had four additional bait sticks per acre placed in the field on June 29. No weevils or weevil damage was observed at Quincey during the season and no weevils were caught in the traps for five weeks, until the middle of August.

The foregoing detailed descriptions and examples are given merely for purposes of illustration. Modifications and variations may be made therein without departing from the spirit and scope of the invention.

INDEX OF ELEMENTS DESIGNATED BY A NUMERAL 1 substrate
3 first end of substrate
5 ground
7 coating
9 cap
11 second end of substrate

We claim:

1. An article of manufacture for controlling insect pests comprising a substrate having thereon a friable coating of a composition comprising:

from about 17% to about 35% by weight of a binder, from about 1% to about 12% by weight of an insect attracting pigment, from about 0.1% to about 4.6% by weight of an insect toxicant, from about 1% to about 23% by weight of an insect feeding stimulant, and from about 1% to about 17% by weight of an ingredient which is both a filler and a thickener.

2. An article of manufacture for controlling insect pests comprising a substrate having thereon a friable coating of a composition comprising:

a binder, an insect attracting pigment, an insect toxicant, a toxicant regeneration enhancer, and an ingredient which is both a filler and a thickener.

3. An article of manufacture for controlling insect pests comprising a substrate having thereon a friable coating of a composition comprising:

from about 17% to about 35% by weight shellac, from about 23% to about 64% by weight ethyl alcohol, from about 1% to about 12% by weight green pigment, from about 0.1% to about 4.6% by weight of an insect toxicant, from about 1% to about 23% by weight crude cottonseed oil, and from about 1% to about 17% by weight clay filler.

4. An article of manufacture for controlling insect pests comprising a substrate having thereon a friable coating of a composition comprising:

from about 23% to about 34% by weight shellac, from about 45% to about 57% by weight ethyl alcohol, from about 4% to about 7% by weight green pigment, from about 0.1% to about 1.7% by weight insect toxicant, from about 1% to about 3% by weight crude cottonseed oil, and from about 5% to about 17% by weight clay filler.

5. An article of manufacture for controlling insect pests comprising a substrate having thereon a friable coating of a composition comprising:

from about 24% to about 31% by weight shellac, from about 47% to about 57% by weight ethyl alcohol, from about 6% to about 7% by weight green pigment, from about 0.14% to about 1.7% by weight insect toxicant, from about 2.4% to about 3% by weight crude cottonseed oil, and from about 9.5% to about 14.3% by weight clay filler.

6. An article of manufacture for controlling insect pests comprising a substrate having thereon (1) a coating of a composition comprising a binder, a pigment, an insect toxicant, an insect feeding stimulant, and an ingredient which is both a filler and a thickener; and (2) a bait composition comprising a polymer, at least one insect pheromone, at least one insect feeding stimulant, and an insect toxicant;

wherein said substrate is a cylinder, and said bait composition is a cap positioned on one end of said substrate.

7. An article of manufacture for controlling insect pests comprising a substrate having thereon a friable coating of a composition comprising from about 17% to about 35% by weight of a binder, from about 1% to about 12% by weight of an insect attracting pigment, from about 0.1% to about 4.6% by weight of an insect toxicant, from about 1% to about 23% by weight of an insect feeding stimulant, from about 1% to about 17% by weight of an ingredient which is both a filler and a thickener;

wherein said substrate is cylindrical in shape and has an outer diameter of from about ⅕ inch to about 1½ inches and is from about 2 feet to about 4 feet in length.

8. An article of manufacture for controlling insect pests comprising a substrate having thereon a friable coating of a composition comprising:

a binder, an insect attracting pigment, an insect toxicant, a toxicant regeneration enhancer, and an ingredient which is both a filler and a thickener;

wherein said substrate has a bait insecticide composition comprising a polymer, at least one insect pheromone, at least one insect feeding stimulant, and an insect toxicant; and said substrate is a cylinder which has an outer diameter of from about ⅕ inch to about 1½ inches and has a length of from about 2 feet to about 4 feet.

9. The article of manufacture of claim 1 wherein said composition further comprises a composition which is an insect attractant.

10. The article of manufacture of claim 1 wherein said composition further includes sufficient solvent to solubilize said ingredient which is both a filler and a thickener.

11. The article of manufacture of claim 10 wherein said solvent is selected from the group consisting of ethyl alcohol, methyl alcohol, chlorinated hydrocarbons, petroleum solvents, turpentine, xylene, and mixtures thereof.

12. The article of manufacture of claim 9 wherein said insect attractant composition is selected from the group consisting of insect pheromones, cotton plant extracts, volatile plant compositions, synthetic insect attractants, and mixtures thereof.

13. The article of manufacture of claims 1, 32, 33, or 35 wherein said insect feeding stimulant is selected from the group consisting of crude cottonseed oil, fatty acid esters of phytol, fatty acid esters of geranyl geraniol, cotton plant extracts, and mixtures thereof.

14. The article of manufacture of claim 1 wherein said ingredient which is both a filler and thickener is an organic composition selected from the group consisting of methyl cellulose, ethyl cellulose, and mixtures thereof.

15. The article of manufacture of claim 1 wherein said insect toxicant is selected from the group consisting of pyrethroid insecticides, organophosphorous insecticides, and mixtures thereof.

16. The article of manufacture of claim 2 wherein said coating composition further includes sufficient solvent to solubilize said ingredient which is both a filler and a thickener.

17. The article of manufacture of claim 16 wherein said solvent is selected from the group consisting of ethyl alcohol, methyl alcohol, chlorinated hydrocarbons, petroleum solvents, turpentine, xylene, and mixtures thereof.

18. The article of manufacture of claim 16 wherein said coating composition further includes an insect attractant.

19. The article of manufacture of claim 18 wherein said attractant is selected from the group consisting of insect pheromones, cotton plant extracts, volatile plant compositions, synthetic insect attractants, and mixtures thereof.

20. The article of manufacture of claim 16 wherein said coating composition comprises from about 10% to about 35% by weight shellac, from about 23% to about 64% by weight ethyl alcohol, from about 1% to about 12% by weight green pigment, from about 0.10% to about 4.6% by weight insect toxicant, from about 1% to about 23% by weight insect toxicant regeneration enhancer, and from about 1% to about 20% by weight clay filler.

21. The article of manufacture of claim 20 wherein said coating composition comprises from about 15% to about 34% by weight shellac, from about 45% to about 57% by weight ethyl alcohol, from about 4% to about 7% by weight green pigment from about 0.1% to about 1.7% by weight insect toxicant, from about 1% to about 23% by weight insect toxicant regeneration enhancer, and from about 5% to about 18% by weight clay filler.

22. The article of manufacture of claim 21 wherein said coating composition comprises from about 15% to about 31% by weight shellac, from about 48% to about 57% by weight ethyl alcohol, from about 6% to about 7% by weight green pigment from about 0.14% to about 1.7% by weight insect toxicant, from about 10% to about 20% by weight insect toxicant regeneration enhancer, and from about 9.5% to about 18% by weight clay filler.

23. The article of manufacture of claim 2 wherein said substrate has thereon a bait insecticide composition comprising a polymer, at least one insect pheromone, at least one insect feeding stimulant, and an insect toxicant.

* * * * *